(12) United States Patent
Ogawa et al.

(10) Patent No.: US 8,025,703 B2
(45) Date of Patent: Sep. 27, 2011

(54) TWO-PART FOAM HAIR DYE

(75) Inventors: Toshio Ogawa, Tokyo (JP); Yoshinori Saito, Tokyo (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 12/995,378

(22) PCT Filed: May 29, 2009

(86) PCT No.: PCT/JP2009/002383
§ 371 (c)(1),
(2), (4) Date: Nov. 30, 2010

(87) PCT Pub. No.: WO2009/144952
PCT Pub. Date: Dec. 3, 2009

(65) Prior Publication Data
US 2011/0073128 A1    Mar. 31, 2011

(30) Foreign Application Priority Data

May 30, 2008    (JP) .................................. 2008-143007

(51) Int. Cl.
*A61Q 5/10*    (2006.01)
(52) U.S. Cl. .............. 8/405; 8/406; 8/424; 8/435; 8/477; 8/526; 8/554
(58) Field of Classification Search .............. 8/405, 406, 8/424, 435, 477, 526, 554
See application file for complete search history.

(56) References Cited

U.S. PATENT DOCUMENTS

| 2004/0213752 A1* | 10/2004 | Fujinuma et al. ............ 424/70.1 |
| 2010/0126522 A1 | 5/2010 | Fujinuma et al. |
| 2010/0126523 A1 | 5/2010 | Fujinuma et al. |
| 2010/0236570 A1 | 9/2010 | Fujinuma et al. |
| 2010/0242187 A1 | 9/2010 | Miyabe |
| 2010/0251488 A1 | 10/2010 | Fujinuma et al. |
| 2010/0257677 A1 | 10/2010 | Miyabe et al. |
| 2010/0299848 A1 | 12/2010 | Fujinuma et al. |
| 2010/0313905 A1 | 12/2010 | Fujinuma et al. |
| 2010/0316583 A1 | 12/2010 | Fujinuma et al. |

FOREIGN PATENT DOCUMENTS

| JP | 2003 40747 | 2/2003 |
| JP | 2004 339216 | 12/2004 |
| JP | 2006 124279 | 5/2006 |
| JP | 2007 291015 | 11/2007 |
| JP | 2007 291016 | 11/2007 |
| JP | 2007 314523 | 12/2007 |
| JP | 2007 314524 | 12/2007 |

OTHER PUBLICATIONS

International Search Report issued Jul. 28, 2009 in PCT/JP09/02383 filed May 29, 2009.

* cited by examiner

*Primary Examiner* — Eisa B Elhilo
(74) *Attorney, Agent, or Firm* — Oblon, Spivak, McClelland, Maier & Neustadt, L.L.P.

(57) ABSTRACT

A two-part foam hair dye having a first agent containing an alkali agent, a second agent containing hydrogen peroxide, and a non-aerosol foamer container, wherein the first agent contains (A), from 0.20 to 2.00 mol/kg of (B), and 0.05 mol/kg or greater of (C1); a total concentration of (C1) and (C2) in the first agent is from 0.16 to 0.50 mol/kg: and a mixture of the first agent and the second agent has a viscosity of from 1 to 300 mPa·s;

(A) a water-soluble cationic polymer,
(B) an alkali metal ion,
(C1) an oxidation dye having a phenolic hydroxyl group, and
(C2) an anionic surfactant.

20 Claims, 1 Drawing Sheet

[FIG. 1]
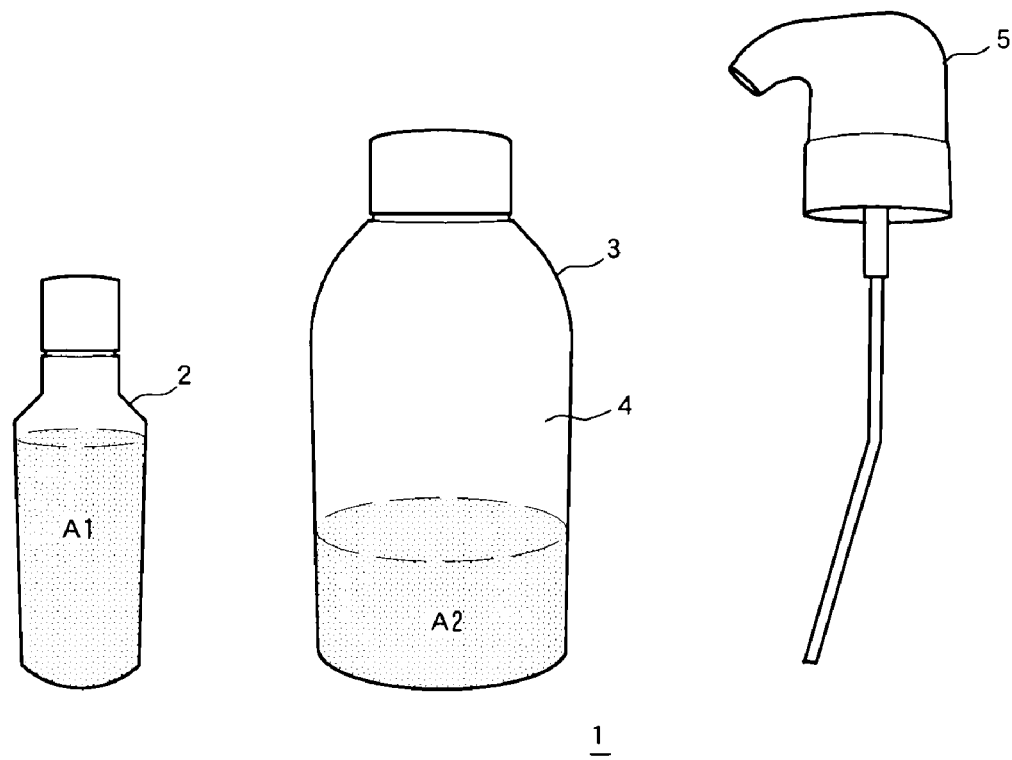
[FIG. 2]
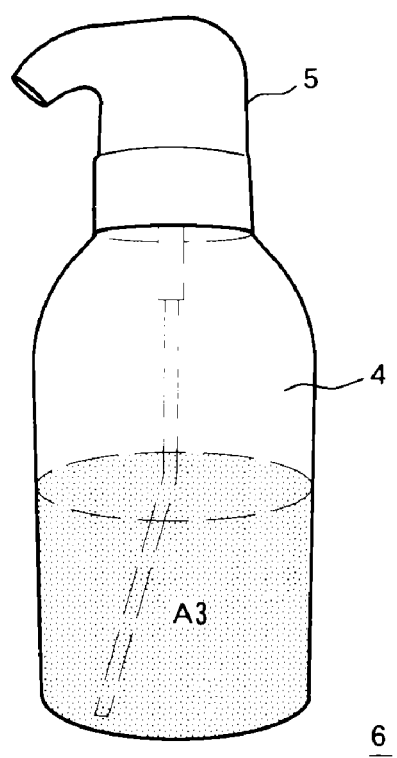

TWO-PART FOAM HAIR DYE

FIELD OF THE INVENTION

The present invention relates to a two-part foam hair dye.

BACKGROUND OF THE INVENTION

Two-part foam hair dyes facilitate a dyeing operation by discharging, in foams, a mixture of a first agent containing an alkali agent and an oxidation dye and a second agent containing an oxidation agent. Compared with one-part foam hair dyes, two-part foam hair dyes can achieve a high hair dyeing effect by only one dyeing operation. Of two-part foam hair dyes, an aerosol type has such problems that it may cause uneven bleaching or uneven dyeing; a pressure container or the like made of a metal is oxidized and corroded by hydrogen peroxide; and an inner pressure of the pressure container increases excessively due to decomposition of hydrogen peroxide.

There are, on the other hand, proposed two-part hair dyes dischargeable in foams from a non-aerosol foamer container (refer to Patent Documents Nos. 1 to 6). Use of them ensures a uniform-color finish because the mixture of the first agent and the second agent can be applied uniformly to the hair. In particular, they are effective for eliminating a difference in color between a newly grown portion and an already dyed portion.

Non-aerosol two-part foam hair dyes should contain a substantial amount of a water-soluble cationic polymer in order to improve lathering and prevent dripping. On the other hand, dyes for gray hair sometimes contain a high concentration of oxidation dyes. Of oxidation dyes, those having a phenolic hydroxyl group are important oxidation dyes inevitable for providing various colors.

PRIOR ART DOCUMENTS

Patent Documents
[Patent Document No. 1] JP-A-2004-339216
[Patent Document No. 2] JP-A-2006-124279
[Patent Document No. 3] JP-A-2007-291015
[Patent Document No. 4] JP-A-2007-291016
[Patent Document No. 5] JP-A-2007-314524
[Patent Document No. 6] JP-A-2007-314523

SUMMARY OF THE INVENTION

In the present invention, there is provided a two-part foam hair dye having a first agent containing an alkali agent, a second agent containing hydrogen peroxide, and a non-aerosol foamer container for discharging, in foams, a mixture of the first agent and the second agent, wherein the first agent contains components (A), (B), and (C1) and optionally contains component (C2); a total concentration of components (C1) and (C2) in the first agent is from 0.16 to 0.50 mol/kg; and the mixture has a viscosity at 25° C. of from 1 to 300 mPa·s:

(A) a water-soluble cationic polymer;
(B) from 0.20 to 2.00 mol/kg of an alkali metal ion;
(C1) 0.05 mol/kg or greater of an oxidation dye having a phenolic hydroxyl group; and
(C2) an anionic surfactant.

BRIEF DESCRIPTION OF DRAWINGS

FIG. 1 illustrates a state, before mixing, of a two-part hair dye composition employed in Examples and Comparative Examples.

FIG. 2 illustrates a state, after mixing, of the two-part hair dye composition employed in Examples and Comparative Examples.

DETAILED DESCRIPTION OF THE INVENTION

It has been found as a result of investigation that when the first agent of a non-aerosol two-part foam hair dye contains a water-soluble cationic polymer and an oxidation dye having a high-concentration of a phenolic hydroxyl group, the water-soluble cationic polymer forms a complex with the oxidation dye, causing the following problems:

1) A complex formed in the first agent impairs storage stability thereof.
2) Since the complex is also present in the mixture of the first agent and the second agent, it deteriorates a discharging property of the mixture from the non-aerosol foamer container.

Accordingly, the present invention relates to a two-part foam hair dye excellent in storage stability and a discharging property of a mixture from a non-aerosol foamer container, though containing a water-soluble cationic polymer and an oxidation dye having a high-concentration of a phenolic hydroxyl group.

The present inventors have found that addition of a specific amount of an alkali metal ion to a two-part foam hair dye prevents formation of a complex, improves the storage stability of the first agent and discharging property of the mixture and moreover, improves a hair dyeing property. The alkali metal ion described above is a component known to prevent swelling of the hair (refer to, for example, page 436 of "Chemical and physical behavior of human hair $4^{th}$ Edition" published in 2002, written by Clarence R. Robbins, published by Springer-Verlag Hew York, Inc.). Since hair dyeing occurs by penetration of a hair dye into the swelled hair, it is surprising that incorporation of a swelling-preventive component such as alkali metal ion has an improving effect of a hair dyeing property.

[Alkali Agent]

As the alkali agent contained in the first agent, ammonia, alkanolamines such as monoethanolamine, sodium hydroxide, potassium hydroxide, and the like can be used. In addition, ammonium salts such as ammonium hydrogen carbonate, ammonium carbonate, and ammonium chloride, and carbonates salts such as potassium carbonate and sodium hydrogen carbonate can be added as a buffer as needed.

The mixture of the first agent and the second agent in the two-part foam hair dye of the present invention has a pH of preferably from 8 to 11, more preferably from 8.5 to 10.5. The using amount of the alkali agent is adjusted as needed so that the pH of the mixture falls within the above range.

[Hydrogen Peroxide]

The content of hydrogen peroxide in the second agent is preferably from 1 to 9 mass %, more preferably from 3 to 6 mass %. The content of hydrogen peroxide in the mixture of the first agent and the second agent is preferably from 1 to 6 mass %, more preferably from 2 to 5 mass %. The pH of the second agent is adjusted to preferably from 2 to 6, more preferably from 2.5 to 4 in order to prevent decomposition of hydrogen peroxide during storage.

[(A): Water-Soluble Cationic Polymer]

The two-part foam hair dye of the present invention contains, in at least the first agent thereof, a water-soluble cationic polymer. The term "water-soluble cationic polymer" means a water-soluble polymer having a cationic group or a group which may be ionized to be a cationic group and it also includes an amphoteric polymer which becomes cationic as a whole. Examples of the water-soluble cationic polymer include water-soluble polymers each having an amino group or an ammonium group on the side chain of its polymer chain, or having a diallyl quaternary ammonium salt as its structural unit, e.g., cationic celluloses, cationic starches, cationic guar gums, polymers or copolymers of a diallyl quaternary ammonium salt, and quaternized polyvinylpyrrolidones.

Specific examples of the polymers or copolymers of a diallyl quaternary ammonium salt include dimethyl diallyl ammonium chloride polymers (Polyquaternium-6, e.g., "Merquat 100", product of Nalco), dimethyl diallyl ammonium chloride/acrylic acid copolymers (Polyquaternium-22, e.g., "Merquat 280" and "Merquat 295", each product of Nalco), dimethyl diallyl ammonium chloride/acrylamide copolymers (Polyquaternium-7, e.g., "Merquat 550", product of Nalco), and acrylic acid/diallyl quaternary ammonium salt/acrylamide copolymers (Polyquaternium-39, e.g., "Merquat Plus 3331", product of Nalco).

Specific examples of the quaternized polyvinylpyrrolidones include quaternary ammonium salts available from a vinylpyrrolidone (VP)/dimethylaminoethyl methacrylate copolymer and diethyl sulfate (Polyquaternium-11, e.g., "Gafquat 734", "Gafquat 755", and "Gafquat 755N", each product of ISP Japan).

Specific examples of the cationic celluloses include polymers of a quaternary ammonium salt available by adding glycidyl trimethylammonium chloride to hydroxyethyl cellulose (Polyquaternium-10, e.g., "Reoguard G" and "Reoguard GP", each product of Lion Corp. and "Polymer JR-125", "Polymer JR-400", "Polymer JR-30M", "Polymer LR-400", and "Polymer LR-30M", each, product of Amerchol), and hydroxyethyl cellulose/dimethyl diallyl ammonium chloride copolymers (Polyquaternium-4, e.g., "Celquat H-100" and "Celquat L-200" (each, product of National Starch and Chemical).

Of these, Polyquaternium-4, Polyquaternium-6, Polyquaternium-7, Polyquaternium-22, and Polyquaternium-39 are preferred as the polymer having a dimethyldiallylammonium salt structure as the structural unit thereof, with Polyquaternium-6, Polyquaternium-7, Polyquaternium-22, and Polyquaternium-39 being more preferred and Polyquaternium-22 being even more preferred.

Two or more of these water-soluble cationic polymers may be used in combination as Component (A). The content of it (or them) is preferably from 0.02 to 6 mass %, more preferably from 0.1 to 4 mass %, even more preferably from 0.2 to 3 mass % in the first agent from the standpoint of good lathering properties, prevention of dripping, and good discharging property from a foamer container.

[(B): Alkali Metal Ion]

The two-part foam hair dye according to the present invention contains, in at least the first agent thereof, an alkali metal ion from the standpoint of good storage stability of the first agent. In the present invention, the alkali metal ion has a function of preventing formation of a complex between the water-soluble cationic polymer as Component (A) and the oxidation dye having a phenolic hydroxyl group as Component (C1) or the anionic surfactant as Component (C2), thereby improving the storage stability of the first agent and discharging property of the mixture. It is generally said that the presence of an alkali metal ion in hair dyes deteriorates the hair dyeing performance thereof, but in the present invention, it exhibits markedly excellent dyeability for the hair.

Examples of sources of the alkali metal ion include salts such as sodium chloride, potassium chloride, sodium sulfate, sodium sulfite, sodium hydroxide, potassium hydroxide, and tetrasodium edetate, as well as counterions in anionic surfactants which will be described later as Component (C2).

Two or more of these alkali metal ions may be used in combination as Component (B). The content of the alkali metal ion (in terms of ion) in the first agent is adjusted to from 0.20 to 2.00 mol/kg, preferably from 0.30 to 1.50 mol/kg, even more preferably from 0.40 to 1.00 mol/kg from the standpoint of effectively preventing formation of a complex between Component (A) and Component (C1) or Component (C2).

[(C1): Oxidation Dye Having a Phenolic Hydroxyl Group]

The first agent of the two-part foam hair dye according to the present invention contains an oxidation dye having a phenolic hydroxyl group as Component (C1). As described above, the oxidation dye having a phenolic hydroxyl group and serving as Component (C1) forms a complex with the water-soluble cationic polymer as Component (A) so that incorporation of such an oxidation dye in a high concentration deteriorates the storage stability of the first agent or discharging property of the mixture. In the present invention, in spite of incorporation of a high concentration of such Component (C1), a specific concentration of the alkali metal ion, as Component (B), incorporated therewith prevents formation of a complex, thereby contributing to good storage stability and discharging property from a foamer container. Examples of such an oxidation dye include dye precursors such as para-aminophenol, 4-amino-3-methylphenol, 6-amino-3-methylphenol, and ortho-aminophenol and couplers such as resorcin, 2-methylresorcin, meta-aminophenol, 5-amino ortho-cresol, and 5-(2-hydroxyethylamino)-2-methylphenol, and 1-naphthol.

In the two-part foam hair dye according to the present invention, the content of the oxidation hair dye having a phenolic hydroxyl group and serving as Component (C1) in the first agent is adjusted to 0.05 mol/kg or greater, preferably from 0.055 to 0.45 mol/kg, more preferably from 0.06 to 0.40 mol/kg.

The two-part foam hair dye according to the present invention may contain an oxidation dye other than Component (C1) or a direct dye. Examples of the oxidation dye other than Component (C1) include dye precursors such as paraphenylenediamine, toluene-2,5-diamine, N,N-bis(2-hydroxyethyl)paraphenylenediamine, 2-(2-hydroxyethyl)paraphenylenediamine, and 1-hydroxyethyl-4,5-diaminopyrazole and couplers such as metaphenylenediamine and 2,4-diaminophenoxyethanol. Examples of the direct dye include para-nitro-ortho-phenylenediamine, para-nitro-meta-phenylenediamine, Basic Yellow 87, Basic Orange 31, Basic Red 12, Basic Red 51, Basic Blue 99, and Acid Orange 7.

[Surfactant]

A surfactant is added to either one or both of the first agent and the second agent in order to facilitate production of foams and at the same time, stabilize them when the hair cosmetic composition is mixed with the air by means of a foam discharge unit of a foamer container. As the surfactant, anionic surfactants as Component (C2), amphoteric surfactants, and nonionic surfactants are preferred to provide good lathering properties to permit easy application of it to the hair even when the liquid temperature is low or near normal temperature.

Examples of the anionic surfactants as Component (C2) include alkyl sulfates and polyoxyalkylene alkyl sulfates. Their alkyl groups have preferably from 10 to 24 carbon atoms, more preferably from 12 to 18 carbon atoms and they are preferably linear. Of these, polyoxyalkylene alkyl sulfates are preferred, with polyoxyethylene alkyl sulfates being more preferred. Among them, those having an average additional mole number of oxyethylene group from 1 to 10 are preferred, with those from 2 to 5 being more preferred. The anionic surfactant serving as Component (C2) forms, similar to the oxidation dye having a phenolic hydroxyl group and serving as Component (C1), a complex with the water-soluble cationic polymer serving as Component (A) and deteriorates the storage stability of the first agent and discharging property of the mixture. In the present invention, however, presence of the alkali metal ion having a specific concentration as Component (B) enables both good storage stability and discharging property from a foamer container, while preventing the formation of a complex.

As Component (C2), two or more of the anionic surfactants may be used in combination and the content of it or them in the first agent is preferably from 0 to 0.45 mol/kg, more preferably from 0.001 to 0.40 mol/kg, even more preferably from 0.01 to 0.30 mol/kg.

The total concentration of Component (C1) and Component (C2) in the first agent is adjusted to from 0.16 to 0.50 mol/kg, preferably from 0.17 to 0.45 mol/kg, even more preferably from 0.18 to 0.40 mol/kg.

Examples of the amphoteric surfactant include carbobetaine, amidobetaine, sulfobetaine, hydroxysulfobetaine, amidosulfobetaine, phosphobetaine and imidazoline surfactants each having an alkyl, alkenyl or acyl group with from 8 to 24 carbon atoms. Of these, the carbobetaine and sulfobetaine surfactants are preferred. Preferred examples of the amphoteric surfactants include lauramidopropyl betaine, cocamidopropyl betaine, lauryl dimethylaminoacetic acid betaine, and lauryl hydroxysulfobetaine. Two or more of these amphoteric surfactants may be used in combination. The content of the amphoteric surfactant in the mixture of the first agent and the second agent is preferably from 0.001 to 5 mass %, more preferably from 0.002 to 2.5 mass %, even more preferably from 0.003 to 1 mass %.

Examples of the nonionic surfactant include alkyl polyglucosides, polyoxyalkylene alkyl ethers, and alkyl glyceryl ethers. In the alkyl polyglucosides, the alkyl group has preferably from 8 to 18 carbon atoms, more preferably from 8 to 14 carbon atoms, even more preferably from 9 to 11 carbon atoms and it is preferably linear. The glucoside has an average polymerization degree of from 1 to 5, more preferably from 1 to 2. In the polyoxyalkylene alkyl ethers, the alkyl group has preferably from 10 to 22 carbon atoms, more preferably from 12 to 18 carbon atoms and it is preferably linear. Of the polyoxyalkylene alkyl ethers, polyoxyethylene alkyl ethers are more preferred. Among them, the polyoxyethylene alkyl ethers having an average additional mole number of oxyethylene group from 1 to 40 are preferred, with those from 4 to 30 being more preferred. The alkyl glyceryl ethers have an alkyl group with preferably from 8 to 18 carbon atoms, more preferably from 8 to 12 carbon atoms and the alkyl group is preferably branched. Two or more of these nonionic surfactants may be used in combination. The content of it or them in the mixture of the first agent and the second agent is preferably from 0.1 to 20 mass %, more preferably from 0.2 to 15 mass %, even more preferably from 0.3 to 10 mass %.

[Higher Alcohol]

The two-part foam hair dye according to the present invention may contain a higher alcohol in order to improve foam retention and improve a preventive effect of dripping during leaving the hair dye on the hair after application. The higher alcohol has an alkyl or alkenyl group with preferably from 10 to 30 carbon atoms, more preferably from 12 to 24 carbon atoms, even more preferably from 14 to 22 carbon atoms. Among others, those having the alkyl groups are preferred, of which those having the linear alkyl groups are more preferred.

Examples of the higher alcohol include myristyl alcohol, cetyl alcohol, stearyl alcohol, behenyl alcohol, isostearyl alcohol, and oleyl alcohol. Two or more of these higher alcohols may be used in combination.

Two or more of these higher alcohols may be used in combination. The higher alcohol may be incorporated in either one or both of the first agent and the second agent. The content of the higher alcohol in the mixture of the first agent and the second agent is from 0.01 to 0.8 mass %, preferably from 0.1 to 0.7 mass %, even more preferably from 0.2 to 0.6 mass % from the standpoint of not impairing the foaming property at the time when the liquid temperature is low and preventing dripping of the hair dye while it is left on the hair.

[Nonvolatile Hydrophilic Solvent]

Moreover, the two-part foam hair dye of the present invention contains preferably a nonvolatile hydrophilic solvent in the first agent or the second agent. This makes it possible to reduce the irritation to the scalp which will otherwise occur by evaporation of water from the hair dye and concentration of the irritating components such as hydrogen peroxide while the hair dye is left on the hair after application. As the nonvolatile hydrophilic solvent, those having no defoaming action such as polyols and lower (from 1 to 4 carbon atoms) alkyl ethers thereof are preferred. As the polyols, those having from 2 to 6 carbon atoms are preferred. Examples include glycerin, propylene glycol, dipropylene glycol, 1,3-butanediol, ethylene glycol, diethylene glycol, isoprene glycol, and sorbitol. Examples of the lower alkyl ethers of the polyol include mono(lower alkyl)ethers and poly(lower alkyl)ethers (such as di(lower alkyl) ethers) of the above polyols. Of these, monomethyl ethers or monoethyl ethers of the polyol is preferred. Specific examples include ethylene glycol monomethyl ether, ethylene glycol monoethyl ether, diethylene glycol monomethyl ether, and diethylene glycol monoethyl ether. Two or more of these nonvolatile hydrophilic solvents may be used in combination.

The content of the nonvolatile hydrophilic solvent(s) in the mixture of the first agent and the second agent is preferably from 0.01 to 5 mass %, more preferably from 0.1 to 4 mass %, even more preferably from 0.2 to 3 mass % in consideration of an effect of reducing the scalp irritation and retention of a good foam quality even at a low liquid temperature.

[Silicones]

The two-part foam hair dye according to the present invention may further contain silicones. Examples of the silicones usable for it include dimethylpolysiloxane, methylphenylpolysiloxane, polyether-modified silicones, amino-modified silicones, and oxazoline-modified silicone elastomer, and emulsions obtained by dispersing them in water with an aid of a surfactant. Of these, polyether-modified silicones and amino-modified silicones, and emulsions thereof are preferred because they can be dispersed in water stably without using a thickener.

The polyether-modified silicones include end-modified ones and side-chain modified ones, for example, pendant type (comb type), both-end modified type, and one-end modified type. Examples of such modified silicones include dimethylsiloxane/methyl(polyoxyethylene)siloxane copolymer, dimethylsiloxane/methyl(polyoxypropylene)siloxane copolymer, dimethylsiloxane/methyl(polyoxyethylene/polyoxypropylene)siloxane copolymer. The polyether-modified silicones have an HLB of preferably 10 or greater, more preferably from 10 to 18 from the standpoint of compatibility with water. The term "HLB" as used herein means a value determined from a phenol index (phenol index: an index correlated with HLB and is applied to ether-type nonionic surfactants).

The amino-modified silicones are not limited insofar as they have an amino or ammonium group, but amodimethicone is preferred.

The content of the silicone(s) in the mixture of the first agent and the second agent is preferably from 0.01 to 10 mass %, more preferably from 0.1 to 5 mass %, even more preferably from 0.5 to 3 mass % in order to smoothly conform the foams to the hair and add high conditioning effects to the hair.

[Other Components]

The first agent and the second agent may further contain, according to the using purpose, a perfume, a ultraviolet absorber, a metal sequestering agent such as edetic acid, a bactericide, a preservative such as methyl paraoxybenzoate, a stabilizer such as phenacetin, 1-hydroxyethane-1,1-diphosphonic acid, or oxyquinoline sulfate, an organic solvent such as ethanol, benzyl alcohol, or benzyloxyethanol, a water-soluble high-molecular compound such as hydroxyethyl cellulose, and a humectant. The mixture of the first agent and the second agent preferably uses water as a main medium.

The oxidation hair dye composition of the present invention is provided as a two-part oxidation hair dye having a first agent containing an alkali agent and a second agent containing hydrogen peroxide. The term "two-part oxidation hair dye" as used herein embraces a three-part oxidation hair dye for use, as a mixture, the first agent, the second agent, and a third agent containing a persulfate or a third agent containing a conditioning component. The first agent and the second agent are mixed at a mass ratio of preferably from 1:4 to 4:1, more preferably from 1:2 to 2:1.

[Viscosity]

The viscosity of the mixture of the first agent and the second agent is adjusted to from 1 to 300 mPa·s, preferably from 2 to 200 mPa·s, more preferably from 3 to 100 mPa·s, even more preferably from 5 to 30 mPa·s. The term "viscosity" as used herein means a value obtained by rotating the mixture at 60 rpm at 25° C. for one minute by using a B-type rotational viscometer ("Model TV-10"), product of Tokimec Inc., and a Rotor No. 1 or No. 2. When the mixture to be measured has a viscosity less than 100 mPa·s, Rotor No. 1 is used, while when it has a viscosity of from 100 to 499 mPa·s, Rotor No. 2 is used for the measurement. The measurement is performed in a temperature-controlled tank of 25° C. immediately after mixing the first agent with the second agent. A temperature change due to reaction heat should be neglected.

Adjustment of the viscosity of the mixture of the first agent and the second agent to the above range enables a foam volume permitting easy application, prevention of dripping of the mixture from the hair to which it has been applied, and facilitation of squeezing upon discharging foams by using a squeeze foamer. A water-soluble solvent such as ethanol should be added, or the content or kind of the surfactant, polyol, or higher alcohol should be adjusted as needed in order to adjust the viscosity of the mixture to fall within the above range.

[Gas-Liquid Mixing Ratio]

A gas-liquid mixing ratio of the air and the mixture by using a foam discharging unit of a foamer container is preferably from 7 to 40 mL/g, more preferably from 15 to 30 mL/g from the standpoint of conformance to the hair and application ease. The term "gas-liquid mixing ratio" as used herein is a value determined in the following manner.

First, the mass and volume of foams discharged at 25° C. are measured to determine the air-liquid mixing ratio. Described specifically, 100 g of the mixture is poured in an S1 squeeze foamer container (product of Daiwa Can, volume: 210 mL, a net roughness (openings) of the mixing chamber: 150 mesh (150 squares per inch (25.4 mm)) and that of the top: 200 mesh) and from the time when the remaining amount becomes 80 g, 20 g of foams are discharged into a 1000-mL measuring flask. The volume of foams is measured one minute after discharge is started. The volume (mL) of foams thus discharged is divided by the mass, that is, 20 g to determine the gas-liquid mixing ratio (mL/g).

[Foamer Container]

In the present invention, the foamer container is a non-aerosol type container used for mixing the air with the mixture of the first agent and the second agent without using a propellant and discharging the mixture in foams. The use of the foamer container is also effective for preventing the scattering of the hair dye thus discharged. In particular, compared with an aerosol type container, the non-aerosol type container can be produced at a low cost and in addition, it does not require a high-pressure gas as a propellant so that hair dye products can be treated more safely during distribution.

The non-aerosol foamer containers usable in the invention are, for example, known pump foamer containers having a foam discharging unit, squeeze foamer containers, electric beaters, and accumulator type pump foamer containers. More specific examples include "Pump Foamer E3 type" and "Pump Foamer F2 type" [each, product of Daiwa Can, *Food & Packaging* (vol. 35, No. 10, p 588 to 593 (1994); vol. 35, No. 11, p 624 to 627 (1994); vol. 36, No. 3, p 154 to 158 (1995))], "S1 squeeze foamer" (product of Daiwa Can, JP-A-7-215352), an electric beater (product of Panasonic Electric Works), and an air spray foamer (product of Airspray International). As the foamer container for use in the two-part foam hair dye of the present invention, a pump foamer container and a squeeze foamer container are preferred because they are inexpensive and convenient.

The pump foamer container or squeeze foamer container has a foam production portion such as net. It has preferably a thin net because when the mixture of the first agent and the second agent is dried into a solid and causes clogging, the flow of foams upon subsequent discharging time can immediately dissolve the solid and eliminate clogging. In this case, the net has preferably a mesh of from 50 to 280, more preferably from 90 to 250, even more preferably from 130 to 220. The term "mesh" as used herein means the number of openings per inch. Use of a net with a mesh falling within the above range enables creamy foams. Examples of the material of such a net include nylon, polyethylene, polypropylene, polyester, Teflon (trade mark), carbon fiber, and stainless steel. Of these, nylon, polyethylene, polypropylene, and polyester are more preferred, with nylon being even more preferred.

The non-aerosol foamer container to be used in the two-part foam hair dye of the present invention is equipped with at least one net, preferably a plurality of such nets. From the standpoint of economy and stability of foams, it is preferred to place the net at two places, that is, the mixing chamber and the top portion of the foamer container.

Portions (the inner wall of the container, the inner wall of the foam discharging unit, and the like) of the non-aerosol foamer container to be brought into contact with the content are preferably made of a material not corroded by an alkali and hydrogen peroxide and permitting passage of oxygen generated as a result of decomposition of hydrogen peroxide.

The two-part foam hair dye of the present invention having the first agent, the second agent, and the non-aerosol foamer container may be provided as a product form in which the first agent and the second agent are filled in respective containers other than the non-aerosol foamer container and these agents are transferred to the non-aerosol foamer container and mixed with each other upon use; or in which one of the agents is filled in the non-aerosol foamer container and the other agent filled in another container is transferred to the non-aerosol foamer container upon use. In this case, the second agent is preferably filled in a container having a gas permeability, particularly a non-aerosol foamer container made of a material (for example, polyethylene) having an oxygen permeability in order to prevent pressure increase in the container due to oxygen generation by decomposition of hydrogen peroxide. On the other hand, the first agent should be filled in a container resistant to oxygen permeation in order to prevent oxidation of the oxidation dye.

[Using Method]

The hair (particularly, the hair of the head) is preferably combed prior to dyeing with the two-part foam hair dye of the present invention. This can prevent tangling of the hair during the re-foaming treatment so that there is no fear of the mixture scattering. In addition, a blocking operation which is employed conventionally upon application of a hair dye composition is not necessarily performed after combing. This blocking operation is preferably omitted. If this operation is omitted, the application operation of the hair dye composition or re-foaming treatment can be performed more easily. Then, the first agent and the second agent of the two-part hair dye of the present invention are mixed in the non-aerosol foamer container. The mixture discharged from the container in foams may be applied directly to the hair or may be applied to the hair with hands or a tool such as brush. It is more preferred to take the mixture in hands (in gloves) and then apply it to the hair from the standpoint of preventing scattering or dripping of the hair dye.

The hair dye is left for about from 3 to 60 minutes, preferably from about 5 to 45 minutes after application. It is preferred to carry out re-foaming on the hair in order to prevent dripping and sufficiently spread the mixture even to the hair root. The re-foaming may be achieved by injecting a gas, using a tool such as oscillator or brush, or using fingers, but foaming with fingers is more preferred.

The re-foaming may be performed after complete disappearance of foams, during disappearance of foams, or before foams applied to the hair undergo a change; or after completion of the application to an entire target area or during the application. The re-foaming may be successively performed once or intermittently performed a plurality of times.

After these operations, the mixture is washed away. The hair is then shampooed or treated with a conditioner, followed by rinsing with water and drying.

EXAMPLES

Examples 1 to 9 and Comparative Examples 1 to 6

The first agent and the second agent having the compositions (mass %) shown in Tables 1, 3 and 5 were prepared and the mixtures were evaluated as described below.

Evaluation of "Storage Stability of First Agent"

After the first agent thus obtained was stored for a month at −5° C., the appearance of it was visually observed and evaluated in accordance with the following criteria.

Storage Stability of First Agent
A: The agent is transparent.
B: The agent becomes turbid but changes to transparent after storage for one day at 25° C.
C: The agent forms a white precipitate, but the precipitate disappears after storage for one day at 25° C.
D: The agent forms a white precipitate and the white precipitate does not disappear even after storage for one day at 25° C.

Evaluation of "Discharging Property of Mixture", "Lathering Properties", "Retention of Foams", and "Dyeing Property"

As illustrated in FIG. 1, a first container (2) was filled with 40 g of the first agent (A1) and a second container (3) (also serving as a squeeze container body (4); internal volume of 210 mL) was filled with 60 g of the second agent (A2). In addition, a squeeze foamer (5) ("S1 Squeeze Foamer" manufactured by Daiwa Can, having a net of 150 mesh in the mixing chamber and a net of 200 mesh at the top of the foamer, each net made of nylon) was prepared.

The first agent and the second agent were filled in the container body (4) at a ratio of 1:1.5 (mass ratio) as illustrated in FIG. 2. The mixture was emitted in foams from the foamer container and the following evaluation was performed.

Discharging Property of Mixture
A: Foam is discharged smoothly even by light pressing of the foamer container.
B: Foam is discharged by strong pressing of the foamer container.
C: Almost no foam is discharged even by strong pressing of the foamer container.
D: No foam is discharged even by strong pressing of the foamer container.

Lathering Properties
A: Foam is very uniform and fine.
B: Foam is uniform and fine.
C: Foam is not uniform and rough.
D: Excess water content prevents formation of foam.

Retention of Foam
A: Foam remains even when it is left on the hair after application and thus shows very high retention.
B: Foam remains for a while even after application and thus shows adequate retention.
C: Foam can be retained without a problem in application, but disappears soon after application.
D: Foam disappears soon after discharging and sometimes causes dripping during application.

Dyeing Property

Each dye was evaluated for its dyeing property by dyeing a tress of goat hair therewith. Described specifically, a tress of goat hair (product of Beaulax, 1 g, 10 cm) was dyed by applying 0.7 g of discharged foam to the tress, leaving it for 30 minutes in a temperature-controlled tank of 30° C., rinsing it with water, and shampooing. The ΔE of the tress between before dyeing and after dyeing was measured (N=1) by using a colorimeter ("CR-400", product of Konica Minolta) and the results are shown in the bottom column of Tables 1 and 2.

Evaluation results, together with the concentration of components and viscosity of the mixture in each formulation, are shown in Tables 2, 4, and 6.

TABLE 1

| | (Mass %; active amount unless indicated by percentage) | Molecular weight | Example 1 | Comp. Ex. 1 |
|---|---|---|---|---|
| | ♦First agent | | | |
| A | Dimethyldiallylammonium chloride/acrylic acid copolymer [*1] | | 0.40 | 0.40 |
| A | Dimethyldiallylammonium chloride/acrylamide copolymer [*2] | | 1.00 | 1.00 |
| A | Dimethyldiallylammonium chloride polymer | | 0.80 | 0.80 |

TABLE 1-continued

| | (Mass %; active amount unless indicated by percentage) | Molecular weight | Example 1 | Comp. Ex. 1 |
|---|---|---|---|---|
| B | Tetrasodium edetate dihydrate | 416.20 | 0.10 | 0.10 |
| B | Sodium sulfite | 126.04 | 0.50 | 0.50 |
| B | Sodium chloride | 58.44 | 3.00 | — |
| B, C2 | Sodium polyoxyethylene (2) lauryl ether sulfate | 376.48 | 2.70 | 2.70 |
| C1 | Para-aminophenol | 109.13 | 0.20 | 0.20 |
| C1 | Resorcinol | 110.11 | 2.00 | 2.00 |
| C1 | Meta-aminophenol | 109.13 | 0.10 | 0.10 |
| C1 | 5-Amino ortho cresol | 123.16 | 0.10 | 0.10 |
| | Toluene-2,5-diamine | | 2.20 | 2.20 |
| | 2,4-Diaminophenoxyethanol hydrochloride | | 0.10 | 0.10 |
| | Decyl (1,4)polyglucoside | | 6.20 | 6.20 |
| | Polyoxyethylene (9) tridecyl ether | | 0.50 | 0.50 |
| | Polyoxyethylene (23) lauryl ether | | 2.00 | 2.00 |
| | Myristyl alcohol | | 0.20 | 0.20 |
| | Ethanol | | 10.00 | 10.00 |
| | Propylene glycol | | 4.00 | 4.00 |
| | Ascorbic acid | | 0.40 | 0.40 |
| | Ammonium hydroxide (28%) | | 3.00 | 3.00 |
| | Ammonium hydrogen carbonate | | 2.50 | 2.50 |
| | Perfume | | 0.80 | 0.80 |
| | Water | | Balance | Balance |
| | ♦Second agent | | | |
| | Aqueous hydrogen peroxide (35%) | | 16.30 | 16.30 |
| B | Sodium hydroxide solution (48%) | 40 | 0.06 | 0.06 |
| B, C2 | Sodium polyoxyethylene (2) lauryl ether sulfate | 376.48 | 0.60 | 0.60 |
| | Cetanol | | 0.48 | 0.48 |
| | Myristyl alcohol | | 0.28 | 0.28 |
| | 1-Hydroxyethane-1,1-diphosphonic acid | | 0.08 | 0.08 |
| | Oxyquinoline sulfate | | 0.04 | 0.04 |
| | Purified water | | Balance | Balance |

[*1] Merquat 280, product of Nalco
[*2] Merquat 550, product of Nalco

TABLE 2

| | | Example 1 | Comp. Ex. 1 |
|---|---|---|---|
| Concentration (mol/kg) of Component (B) in first agent | | 0.67 | 0.16 |
| Concentration (mol/kg) of Component (C1) in first agent | | 0.22 | 0.22 |
| Concentration (mol/kg) of Component (C2) in first agent | | 0.07 | 0.07 |
| Concentration (mol/kg) of Components (C1) and (C2) in first agent | | 0.29 | 0.29 |
| Viscosity of mixture (25° C., mPa · s) | | 15 | 15 |
| Evaluation | Storage stability of first agent | A | D |
| | Discharging property | A | C |
| | Lathering properties | A | C |
| | Foam retention | A | C |
| | Dyeing property (ΔE) | 59.18 | 55.95 |

TABLE 3

| | (Mass %; active amount unless indicated by percentage) | Molecular weight | Examples | | | | | | | |
|---|---|---|---|---|---|---|---|---|---|---|
| | | | 2 | 3 | 4 | 5 | 6 | 7 | 8 | 9 |
| | First agent | | | | | | | | | |
| A | Dimethyldiallylammonium chloride/acrylic acid copolymer[*1] | | 0.40 | 0.40 | 0.40 | 0.40 | 0.40 | 0.40 | 0.40 | 0.40 |
| A | Dimethyldiallylammonium chloride/acrylamide copolymer[*2] | | 1.00 | 1.00 | 1.00 | 1.00 | 1.00 | 1.00 | 1.00 | 1.00 |
| B | Tetrasodium edetate dihydrate | 416.20 | 0.10 | 0.10 | 0.10 | 0.10 | 0.10 | 0.10 | 0.10 | 0.10 |
| B | Sodium sulfite | 126.04 | 0.50 | 0.50 | 0.50 | 0.50 | 0.50 | 0.50 | 0.50 | 0.50 |
| B | Sodium chloride | 58.44 | 0.50 | 1.50 | 3.00 | 6.00 | 10.00 | — | — | 0.80 |
| B | Potassium chloride | 74.55 | — | — | — | — | — | 1.90 | — | 0.90 |
| B | Sodium sulfate | 142.04 | — | — | — | — | — | — | 1.80 | — |
| B, C2 | Sodium polyoxyethylene (2) lauryl ether sulfate | 376.48 | 2.70 | 2.70 | 2.70 | 2.70 | 2.70 | 2.70 | 2.70 | 2.70 |
| C1 | Para-aminophenol | 109.13 | 0.20 | 0.20 | 0.20 | 0.20 | 0.20 | 0.20 | 0.20 | 0.20 |
| C1 | Resorcinol | 110.11 | 2.00 | 2.00 | 2.00 | 2.00 | 2.00 | 2.00 | 2.00 | 2.00 |
| C1 | Meta-aminophenol | 109.13 | 0.10 | 0.10 | 0.10 | 0.10 | 0.10 | 0.10 | 0.10 | 0.10 |

TABLE 3-continued

| | (Mass %; active amount unless indicated by percentage) | Molecular weight | Examples 2 | 3 | 4 | 5 | 6 | 7 | 8 | 9 |
|---|---|---|---|---|---|---|---|---|---|---|
| C1 | 5-Amino ortho cresol | 123.16 | 0.10 | 0.10 | 0.10 | 0.10 | 0.10 | 0.10 | 0.10 | 0.10 |
| | Toluene-2,5-diamine | | 2.20 | 2.20 | 2.20 | 2.20 | 2.20 | 2.20 | 2.20 | 2.20 |
| | 2,4-Diaminophenoxyethanol hydrochloride | | 0.10 | 0.10 | 0.10 | 0.10 | 0.10 | 0.10 | 0.10 | 0.10 |
| | Decyl (1,4)polyglucoside | | 6.20 | 6.20 | 6.20 | 6.20 | 6.20 | 6.20 | 6.20 | 6.20 |
| | Polyoxyethylene (9) tridecyl ether | | 0.50 | 0.50 | 0.50 | 0.50 | 0.50 | 0.50 | 0.50 | 0.50 |
| | Polyoxyethylene (23) lauryl ether | | 2.00 | 2.00 | 2.00 | 2.00 | 2.00 | 2.00 | 2.00 | 2.00 |
| | Myristyl alcohol | | 0.20 | 0.20 | 0.20 | 0.20 | 0.20 | 0.20 | 0.20 | 0.20 |
| | Ethanol | | 10.00 | 10.00 | 10.00 | 10.00 | 10.00 | 10.00 | 10.00 | 10.00 |
| | Propylene glycol | | 4.00 | 4.00 | 4.00 | 4.00 | 4.00 | 4.00 | 4.00 | 4.00 |
| | Ascorbic acid | | 0.40 | 0.40 | 0.40 | 0.40 | 0.40 | 0.40 | 0.40 | 0.40 |
| | Ammonium hydroxide (28%) | | 3.00 | 3.00 | 3.00 | 3.00 | 3.00 | 3.00 | 3.00 | 3.00 |
| | Ammonium hydrogen carbonate | | 2.50 | 2.50 | 2.50 | 2.50 | 2.50 | 2.50 | 2.50 | 2.50 |
| | Perfume | | 0.80 | 0.80 | 0.80 | 0.80 | 0.80 | 0.80 | 0.80 | 0.80 |
| | Water | | Balance | Balance | Balance | Balance | Balance | Balance | Balance | Balance |
| | Second agent | | | | | | | | | |
| | Aqueous hydrogen peroxide (35%) | | 16.30 | 16.30 | 16.30 | 16.30 | 16.30 | 16.30 | 16.30 | 16.30 |
| B | Sodium hydroxide solution (48%) | 40 | 0.06 | 0.06 | 0.06 | 0.06 | 0.06 | 0.06 | 0.06 | 0.06 |
| B, C2 | Sodium polyoxyethylene (2) lauryl ether sulfate | 376.48 | 0.60 | 0.60 | 0.60 | 0.60 | 0.60 | 0.60 | 0.60 | 0.60 |
| | Cetanol | | 0.48 | 0.48 | 0.48 | 0.48 | 0.48 | 0.48 | 0.48 | 0.48 |
| | Myristyl alcohol | | 0.28 | 0.28 | 0.28 | 0.28 | 0.28 | 0.28 | 0.28 | 0.28 |
| | 1-Hydroxyethane-1,1-diphosphonic acid | | 0.08 | 0.08 | 0.08 | 0.08 | 0.08 | 0.08 | 0.08 | 0.08 |
| | Oxyquinoline sulfate | | 0.04 | 0.04 | 0.04 | 0.04 | 0.04 | 0.04 | 0.04 | 0.04 |
| | Purified water | | Balance | Balance | Balance | Balance | Balance | Balance | Balance | Balance |

[1]Merquat 280, product of Nalco
[2]Merquat 550, product of Nalco

TABLE 4

| | | Examples 2 | 3 | 4 | 5 | 6 | 7 | 8 | 9 |
|---|---|---|---|---|---|---|---|---|---|
| Concentration (mol/kg) of Component (B) in first agent | | 0.25 | 0.42 | 0.67 | 1.19 | 1.87 | 0.42 | 0.41 | 0.42 |
| Concentration (mol/kg) of Component (C1) in first agent | | 0.22 | 0.22 | 0.22 | 0.22 | 0.22 | 0.22 | 0.22 | 0.22 |
| Concentration (mol/kg) of Component (C2) in first agent | | 0.07 | 0.07 | 0.07 | 0.07 | 0.07 | 0.07 | 0.07 | 0.07 |
| Concentration (mol/kg) of Components (C1) and (C2) in first agent | | 0.29 | 0.29 | 0.29 | 0.29 | 0.29 | 0.29 | 0.29 | 0.29 |
| Viscosity of mixture (25° C., mPa·s) | | 10 | 10 | 10 | 10 | 10 | 10 | 10 | 10 |
| Evaluation | Storage stability of first agent | B | A | A | A | B | A | A | A |
| | Discharging property | A | A | A | A | A | A | A | A |
| | Lathering properties | A | A | A | A | A | A | A | A |
| | Foam retention | A | A | A | A | A | A | A | A |
| | Dyeing property (ΔE) | 59.06 | 57.70 | 58.38 | 57.96 | 59.60 | 59.85 | 59.23 | 59.02 |

TABLE 5

| | (Mass %; active amount unless indicated by percentage) | Molecular weight | Comparative Examples 2 | 3 | 4 | 5 | 6 |
|---|---|---|---|---|---|---|---|
| | First agent | | | | | | |
| A | Dimethyldiallylammonium chloride/acrylic acid copolymer[1] | | — | 0.40 | 0.40 | 0.40 | 0.40 |
| A | Dimethyldiallylammonium chloride/acrylamide copolymer[2] | | — | 1.00 | 1.00 | 1.00 | 1.00 |
| B | Tetrasodium edetate dihydrate | 416.20 | 0.10 | 0.10 | 0.10 | 0.10 | 0.10 |
| B | Sodium sulfite | 126.04 | 0.50 | 0.50 | 0.50 | 0.50 | 0.50 |
| B | Sodium chloride | 58.44 | 1.50 | — | 12.00 | 1.50 | 1.50 |

TABLE 5-continued

| | (Mass %; active amount unless indicated by percentage) | Molecular weight | Comparative Examples | | | | |
|---|---|---|---|---|---|---|---|
| | | | 2 | 3 | 4 | 5 | 6 |
| B | Potassium chloride | 74.55 | — | — | — | — | — |
| B | Sodium sulfate | 142.04 | — | — | — | — | — |
| B, C2 | Sodium polyoxyethylene (2) lauryl ether sulfate | 376.48 | 2.70 | 2.70 | 2.70 | 15.00 | 2.70 |
| C1 | Para-aminophenol | 109.13 | 0.20 | 0.20 | 0.20 | 0.20 | 1.50 |
| C1 | Resorcinol | 110.11 | 2.00 | 2.00 | 2.00 | 2.00 | 2.50 |
| C1 | Meta-aminophenol | 109.13 | 0.10 | 0.10 | 0.10 | 0.10 | 1.50 |
| C1 | 5-Amino ortho cresol | 123.16 | 0.10 | 0.10 | 0.10 | 0.10 | 1.00 |
| | Toluene-2,5-diamine | | 2.20 | 2.20 | 2.20 | 2.20 | 3.00 |
| | 2,4-Diaminophenoxyethanol hydrochloride | | 0.10 | 0.10 | 0.10 | 0.10 | 0.10 |
| | Decyl (1,4)polyglucoside | | 6.20 | 6.20 | 6.20 | 6.20 | 6.20 |
| | Polyoxyethylene (9) tridecyl ether | | 0.50 | 0.50 | 0.50 | 0.50 | 0.50 |
| | Polyoxyethylene (23) lauryl ether | | 2.00 | 2.00 | 2.00 | 2.00 | 2.00 |
| | Myristyl alcohol | | 0.20 | 0.20 | 0.20 | 0.20 | 0.20 |
| | Ethanol | | 10.00 | 10.00 | 10.00 | 10.00 | 10.00 |
| | Propylene glycol | | 4.00 | 4.00 | 4.00 | 4.00 | 4.00 |
| | Ascorbic acid | | 0.40 | 0.40 | 0.40 | 0.40 | 0.40 |
| | Ammonium hydroxide (28%) | | 3.00 | 3.00 | 3.00 | 3.00 | 3.00 |
| | Ammonium hydrogen carbonate | | 2.50 | 2.50 | 2.50 | 2.50 | 2.50 |
| | Perfume | | 0.80 | 0.80 | 0.80 | 0.80 | 0.80 |
| | Water | | Balance | Balance | Balance | Balance | Balance |
| | Second agent | | | | | | |
| | Aqueous hydrogen peroxide (35%) | | 16.30 | 16.30 | 16.30 | 16.30 | 16.30 |
| B | Sodium hydroxide solution (48%) | 40 | 0.06 | 0.06 | 0.06 | 0.06 | 0.06 |
| B, C2 | Sodium polyoxyethylene (2) lauryl ether sulfate | 376.48 | 0.60 | 0.60 | 0.60 | 0.60 | 0.60 |
| | Cetanol | | 0.48 | 0.48 | 0.48 | 0.48 | 0.48 |
| | Myristyl alcohol | | 0.28 | 0.28 | 0.28 | 0.28 | 0.28 |
| | 1-Hydroxyethane-1,1-diphosphonic acid | | 0.08 | 0.08 | 0.08 | 0.08 | 0.08 |
| | Oxyquinoline sulfate | | 0.04 | 0.04 | 0.04 | 0.04 | 0.04 |
| | Purified water | | Balance | Balance | Balance | Balance | Balance |

*[1] Merquat 280, product of Nalco
*[2] Merquat 550, product of Nalco

TABLE 6

| | | Comparative Examples | | | | |
|---|---|---|---|---|---|---|
| | | 2 | 3 | 4 | 5 | 6 |
| Concentration (mol/kg) of Component (B) in first agent | | 0.42 | 0.16 | 2.21 | 0.74 | 0.42 |
| Concentration (mol/kg) of Component (C1) in first agent | | 0.22 | 0.22 | 0.22 | 0.22 | 0.58 |
| Concentration (mol/kg) of Component (C2) in first agent | | 0.07 | 0.07 | 0.07 | 0.40 | 0.07 |
| Concentration (mol/kg) of Components (C1) and (C2) in first agent | | 0.29 | 0.29 | 0.29 | 0.62 | 0.65 |
| Viscosity of mixture (25° C., mPa · s) | | 5 | 10 | 10 | 10 | 10 |
| Evaluation | Storage stability of first agent | A | D | D | D | D |
| | Discharging properties | A | C | C | C | C |
| | Lathering property | C | D | D | D | D |
| | Foam retention | D | D | D | D | D |
| | Dyeing property (ΔE) | 55.39 | 55.83 | 55.36 | 56.09 | 64.30 |

[Legend]
1: Each constituent of a two-part hair dye composition
2: First container
3: Second container
4: Body of squeeze container
5: Squeeze foamer
6: Squeeze container
A1: First agent
A2: Second agent
A3: Mixture

What is claimed is:

1. A two-part foam hair dye comprising a first agent comprising an alkali agent, a second agent comprising hydrogen peroxide, and a non-aerosol foamer container for discharging a mixture of the first agent and the second agent in foams, wherein the first agent comprises components (A), (B), and (C1) and optionally component (C2); a total concentration of components (C1) and (C2) in the first agent is from 0.16 to 0.50 mol/kg; the mixture has a viscosity at 25° C. of from 1 to 300 mPa·s:
 (A) a water-soluble cationic polymer;
 (B) from 0.20 to 2.00 mol/kg of an alkali metal ion;
 (C1) 0.05 mol/kg or greater of an oxidation dye having a phenolic hydroxyl group; and
 (C2) an anionic surfactant.

2. The two-part foam hair dye according to claim 1, wherein a content of Component (A) in the first agent is from 0.02 to 6 mass %.

3. The two-part foam hair dye according to claim 1, wherein a content of Component (C2) in the first agent is from 0 to 0.45 mol/kg.

4. The two-part foam hair dye according to claim 1, wherein the mixture of the first agent and the second agent in the two-part foam hair dye of the present invention has a pH of from 8 to 11.

5. The two-part foam hair dye according to claim 1, wherein the component (A) a water-soluble cationic polymer is one or more of polymers selected from the group consisting of Polyquaternium-4, Polyquaternium-6, Polyquaternium-7, Polyquaternium-10, Polyquaternium-11, Polyquaternium-22, and Polyquaternium-39.

6. The two-part foam hair dye according to claim 1, wherein the content of the component (A) in the first agent is from 0.1 to 4 mass%.

7. The two-part foam hair dye according to claim 1, wherein sources of the component (B) an alkali metal ion is one or more compounds selected from the group consisting of sodium chloride, potassium chloride, sodium sulfate, sodium sulfite, sodium hydroxide, potassium hydroxide, tetrasodium edetate, and counterions in anionic surfactants of the Component (C2).

8. The two-part foam hair dye according to claim 1, wherein oxidation dye having a phenolic hydroxyl group of the component (C1) is one or more compounds selected from the group consisting of para-aminophenol, 4-amino-3-methylphenol, 6-amino-3-methylphenol, ortho-aminophenol, resorcin, 2-methylresorcin, meta-aminophenol, 5-amino ortho-cresol, 5-(2-hydroxyethylamino)-2-methylphenol, and 1-naphthol.

9. The two-part foam hair dye according to claim 1, wherein the content of the component (C1) in the first agent is from 0.055 to 0.45 mol/kg.

10. The two-part foam hair dye according to claim 1, wherein the anionic surfactants as Component (C2) is one or more compounds selected from the group consisting of alkyl sulfates and polyoxyalkylene alkyl sulfates.

11. The two-part foam hair dye according to claim 1, wherein the content of the Component (C2) in the first agent is from 0.001 to 0.4O mol/kg.

12. The two-part foam hair dye according to claim 1, wherein from 0.001 to 5 mass% of amphoteric surfactant is further contained in the mixture of the first agent and the second agent.

13. The two-part foam hair dye according to claim 1, wherein from 0.1 to 20 mass% of nonionic surfactant is further contained in the mixture of the first agent and the second agent.

14. The two-part foam hair dye according to claim 1, wherein the viscosity of the mixture of the first agent and the second agent at 25° C. is 2 to 200 mPa·s.

15. The two-part foam hair dye according to claim 1, wherein the viscosity of the mixture of the first agent and the second agent at 25° C. is 3 to 100 mPa·s.

16. A method for hair dye using the two-part foam hair dye according to claim 1, wherein the method comprises the steps of
 the first agent and the second agent are mixed;
 the mixture is discharged from the non-aerosol foamer container in foam;
 the discharged foam is applied to the hair;
 the foam is left for from 3 to 60 minutes; and
 the foam is washed away.

17. The method according to claim 16, wherein the mixture discharged from the container in foam is taken in hands and then applied to the hair.

18. The method according to claim 16, wherein the foam applied to the hair is re-foamed on the hair.

19. The method according to claim 18, wherein the re-foaming is achieved by using fingers.

20. The two-part foam hair dye according to claim 2, wherein a content of Component (C2) in the first agent is from 0 to 0.45 mol/kg.

* * * * *

UNITED STATES PATENT AND TRADEMARK OFFICE
CERTIFICATE OF CORRECTION

PATENT NO.        : 8,025,703 B2                                             Page 1 of 1
APPLICATION NO.   : 12/995378
DATED             : September 27, 2011
INVENTOR(S)       : Toshio Ogawa et al.

It is certified that error appears in the above-identified patent and that said Letters Patent is hereby corrected as shown below:

Column 17, line 20, "0.4O" should read --0.40--.

Signed and Sealed this
Sixth Day of March, 2012

David J. Kappos
*Director of the United States Patent and Trademark Office*